US009279761B1

(12) United States Patent
Sternick (10) Patent No.: US 9,279,761 B1
(45) Date of Patent: Mar. 8, 2016

(54) CUVETTE SYSTEM

(71) Applicant: John L. Sternick, Brandon, SD (US)

(72) Inventor: John L. Sternick, Brandon, SD (US)

( * ) Notice: Subject to any disclaimer, the term of this patent is extended or adjusted under 35 U.S.C. 154(b) by 0 days.

(21) Appl. No.: 14/615,544

(22) Filed: Feb. 6, 2015

(51) Int. Cl.
*G01N 21/03* (2006.01)

(52) U.S. Cl.
CPC .... *G01N 21/0303* (2013.01); *G01N 2021/0389* (2013.01); *G01N 2201/02* (2013.01)

(58) Field of Classification Search
USPC ........... 356/244, 246; 250/576; 422/102, 104, 422/82.09, 547, 561, 562
See application file for complete search history.

(56) References Cited

U.S. PATENT DOCUMENTS

| | | | |
|---|---|---|---|
| 3,556,731 A | 1/1971 | Martin | |
| 4,318,994 A | 3/1982 | Meyer | |
| 4,332,471 A * | 6/1982 | Gross | 356/246 |
| 4,806,316 A | 2/1989 | Johnson | |
| 4,999,285 A | 3/1991 | Stiso | |
| 5,128,104 A | 7/1992 | Murphy | |
| D395,708 S | 6/1998 | Shartle | |
| 5,916,525 A | 6/1999 | Husar | |
| 6,249,345 B1 * | 6/2001 | Kraack et al. | 356/246 |
| 6,589,790 B1 | 7/2003 | Colin | |
| 6,929,158 B2 | 8/2005 | Smiley | |
| 8,537,352 B2 * | 9/2013 | Eikelmann et al. | 356/246 |
| 8,802,029 B2 | 8/2014 | Steinmiller | |
| 2007/0019189 A1 * | 1/2007 | Marsteller et al. | 356/246 |
| 2010/0104475 A1 | 4/2010 | Miyoshi | |
| 2011/0164245 A1 * | 7/2011 | Eikelmann et al. | 356/246 |
| 2011/0170094 A1 * | 7/2011 | Harnack et al. | 356/246 |
| 2012/0322052 A1 | 12/2012 | Halverson | |

FOREIGN PATENT DOCUMENTS

WO    WO 0075632 A1 * 12/2000

* cited by examiner

*Primary Examiner* — Sang Nguyen
(74) *Attorney, Agent, or Firm* — Jeffrey A. Proehl; Woods, Fuller, Shultz & Smith, P.C.

(57) ABSTRACT

A cuvette system may comprise a disposable cuvette element for holding a sample for analysis, with the cuvette element comprising an elongated strip having opposite faces and a well for receiving the sample to be analyzed. The well may be formed on the strip to hold a sample on the strip, and a hole may form at least a portion of the well and may extend through the strip. The well may be configured to hold a defined volume of the sample to be held therein. The system may comprise a reusable holder for removably receiving the cuvette element, with the holder having a substantially hollow interior for receiving at least a portion of the cuvette element. The holder may have a perimeter wall including a front wall and a rear wall of the holder, and a window may be formed in each of the front and rear walls and may be generally positioned in alignment with each other. The windows may be alignable with the well in the cuvette element when the cuvette element is inserted into the holder such that a straight line passes through the windows and the well simultaneously.

19 Claims, 9 Drawing Sheets

CUVETTE SYSTEM

BACKGROUND

Field

The present disclosure relates to cuvettes and more particularly pertains to a new cuvette system that may provide more economical and more accurate testing of samples.

SUMMARY

The present disclosure relates to a cuvette system which may comprise a disposable cuvette element for holding a sample for analysis. The cuvette element may comprise an elongated strip having opposite faces and a well for receiving the sample to be analyzed. The well may be formed on the strip to hold a sample on the strip, and a hole may form at least a portion of the well and may extend through the strip. The well may be configured to hold a defined volume of the sample to be held therein. The system may comprise a reusable holder for removably receiving the cuvette element, with the holder having a substantially hollow interior for receiving at least a portion of the cuvette element. The holder may have a perimeter wall including a front wall and a rear wall of the holder, and a window may be formed in each of the front and rear walls and may be generally positioned in alignment with each other. The windows may be alignable with the well in the cuvette element when the cuvette element is inserted into the holder such that a straight line passes through the windows and the well simultaneously.

There has thus been outlined, rather broadly, some of the more important elements of the disclosure in order that the detailed description thereof that follows may be better understood, and in order that the present contribution to the art may be better appreciated. There are additional elements of the disclosure that will be described hereinafter and which will form the subject matter of the claims appended hereto.

In this respect, before explaining at least one embodiment or implementation in greater detail, it is to be understood that the scope of the disclosure is not limited in its application to the details of construction and to the arrangements of the components, and the particulars of the steps set forth in the following description or illustrated in the drawings. The disclosure is capable of other embodiments and implementations and is thus capable of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

The advantages of the various embodiments of the present disclosure, along with the various features of novelty that characterize the disclosure, are disclosed in the following descriptive matter and accompanying drawings.

BRIEF DESCRIPTION OF THE DRAWINGS

The disclosure will be better understood and when consideration is given to the drawings and the detailed description which follows. Such description makes reference to the annexed drawings wherein.

DETAILED DESCRIPTION

With reference now to the drawings, and in particular to FIGS. 1 through 9 thereof, a new cuvette system embodying the principles and concepts of the disclosed subject matter will be described.

Applicant has recognized at least two problems with existing cuvettes. Generally, cuvettes are constructed of relatively expensive materials such that a cuvette must be reused time and time again, or are entirely disposable after a single use. Reusable cuvettes thus require special and vigorous cleaning to avoid contamination between samples use in subsequent tests, and disposable cuvettes are wasteful and may not provide accurate results. Another problem with existing cuvette designs is that the cuvette encloses or encompasses the sample to such a degree that the analyzing beam of the testing equipment must not only pass through the sample but also through a portion of the material forming the cuvette. This factor requires that an adjustment be taken into consideration in analyzing the results produced by the analyzing machine since the beam is not only passed through the sample material but also through the cuvette material which alters or skews the results of the testing.

In view of these problems, the applicant has devised a cuvette system in which only a portion of the cuvette contacts and holds the sample, and this portion may be economically disposed of so that there is no need to reuse the portion of the cuvette exposed to the sample and thus no need to perform the rigorous cleaning of the cuvette. In the new cuvette system, a significant portion of the cuvette system simply acts as a holder for the disposable portion of the cuvette, and may be reused with other sample holding portions. The interchangeability of the applicant's cuvette system also permits an adjustment of the sample holding portion for a particular sample size to be analyzed so that an entire and separate cuvette is not required for each different sample size. Furthermore, and significantly, embodiments of the cuvette system may be configured such that the beam of energy passing through the sample does not have to pass through the material forming the cuvette, and no adjustment to the results of the analysis needs to be made to account for results produced by the cuvette material. This aspect may greatly simplify the analysis needed for use of the cuvette system as adjustments are not necessary for results changed by the material of the cuvette.

Figure 1:
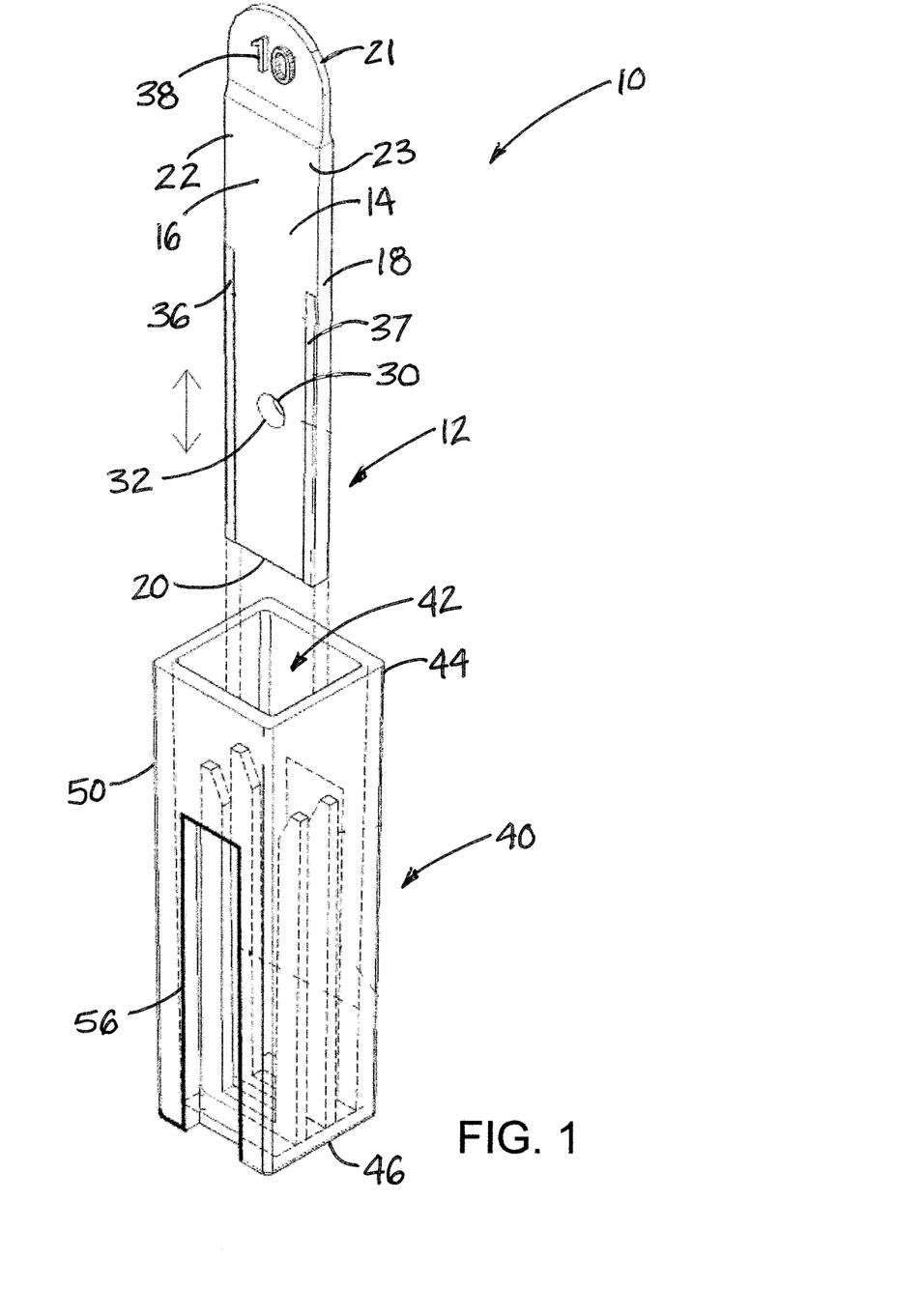
FIG. 1 is a schematic perspective view of a new cuvette system according to the present disclosure in an exploded or disassembled condition.

In one aspect, the disclosure relates to a cuvette system 10 for generally providing the ability to perform various types of analysis, such as spectrophotometric analysis, on a sample without requiring that the cuvette system 10 be entirely discarded, or that some manner of cleaning be applied to the cuvette system. In general, the cuvette system 10 includes a disposable cuvette element 12 for holding a sample to be analyzed, and a reusable holder 40 for removably receiving a cuvette element in a manner suitable for performing an analysis on the sample. In some of the most preferred embodiments, the cuvette element 12 is disposed after it is used to hold a sample, and the holder 40 may be reused with another cuvette element holding another sample.

In greater detail, the cuvette element 12 may include an elongated strip 14 which may have opposite faces 16, 17, and the distance between the faces may define a thickness therebetween. The strip 14 may have a substantially uniform thickness, although strips of non-uniform thickness may also be utilized. The strip 14 may also have a perimeter edge 18 which may be generally rectangular in shape, although in some embodiments such as the illustrative embodiments, one end of the strip intended to be gripped by the fingers of the user may have a rounded or curved profile. The perimeter edge may include a pair of opposite end edge portions 20, 21 including a lower end edge portion 20 and an upper end edge portion 21, and illustratively the lower end edge portion 20 may be substantially linear and straight while the upper edge end portion may have a semicircular or generally rounded shape. The perimeter edge 18 may also include a pair of opposite side edge portions 22, 23 which illustratively are substantially linear and straight and substantially parallel to each other such that the strip has a substantially uniform width between the end edge portions, although other configurations may be utilized.

The cuvette element 12 may also include a well 30 for receiving the sample to be analyzed and holding the sample on the strip as the cuvette element 12 is moved into and out of the holder 40. The well may be configured with a certain size or volume to hold a defined volume of the sample, and the defined size or volume may varied from one element 12 to another element to permit the system to be easily adapted for use the size of the particular sample to be tested. For example, well sizes such as 1 microliter, 2 microliters, 4 micro liters and 10 microliters may be utilized, but other sizes larger, smaller or in between these sizes may also be used. Of course, it will be recognized that despite a defined volume, the sample positioned by the user in the well may be less than or greater than the defined size. A hole 32 may form at least a portion of the well 30, and may extend through the strip 14, such as between the opposite faces 16, 17. The hole of the well may have an area that is sized for defining a particular volume of the sample to be held therein.

In some embodiments, the well may include a wall 34 that may generally extend around the hole 32 and may extend from at least one of the opposite faces of the strip in order to increase the volume of the sample capable of being held in the well 30. In some embodiments, the wall 34 may be generally cylindrical in shape, while in other embodiments the wall may be generally rectangular. With some implementations the rectangular wall may have an open upper side. In the most preferred embodiments, the well provides a space for receiving a sample that is not obstructed by the material forming the well at least along an axis extending perpendicular to the plane of the faces of the elongated strip 14. This permits a beam of light or energy or particles from an analysis machine to pass directly through the sample without also passing through a portion of the cuvette element 12. Further, the position of the well 30 with respect to the strip 14, and more particularly with respect to the lower end edge portion 20, may vary from one strip to another to accommodate the physical configuration of various analysis machines.

In some embodiments of the cuvette element 12, at least one rail 36 may be formed on at least one of the opposite faces of the elongated strip 14, and may protrude from the face for a distance. Some embodiments may include a pair of rails 36, 37 that protrude from the same face of the strip 14 in order to provide a relatively thicker edge thickness relative to the thickness of the majority of the strip. The rails 36, 37 may be substantially linear, and may be formed on one or both faces of the strip. Each of the rails may be positioned along at least a section of one of the side edge portions of the perimeter edge of the strip. In addition to providing a relatively thicker thickness for the cuvette element 12 along the side edge portions of the strip 14, the rails may also provide a degree of resistance to bending of the strip by imparting additional rigidity.

The cuvette element 12 may also include a marking 38 positioned on the strip which provides information to the user including a relative size or capacity of the well directly in a volume measurement or symbolically through the user of letters or numbers or other indicia.

The reusable holder 40 of the cuvette system 10 may be configured for removably receiving a cuvette element 12, and may be intended to be used with a plurality of interchangeable and replaceable elements 12 such that the cuvette element 12 may be disposed of after a single use while the holder 40 continues to be used for many uses with additional cuvette elements. Additionally, the interchangeability of the cuvette element in the holder 40 permits the holder to be used with a variety of different cuvette elements having different sample capacities (and not only a single capacity). The holder 40 may have a substantially hollow interior 42 for receiving at least a portion of the cuvette element (and not necessarily the entire element 12, although that option may be utilized). The holder may be sized such that an upper portion of the cuvette element remains outside of the interior when the element 12 is fully inserted into the holder to provide a finger-gripping location on the element 12 that remains accessible to the user's fingers for removal after use.

Figure 7:
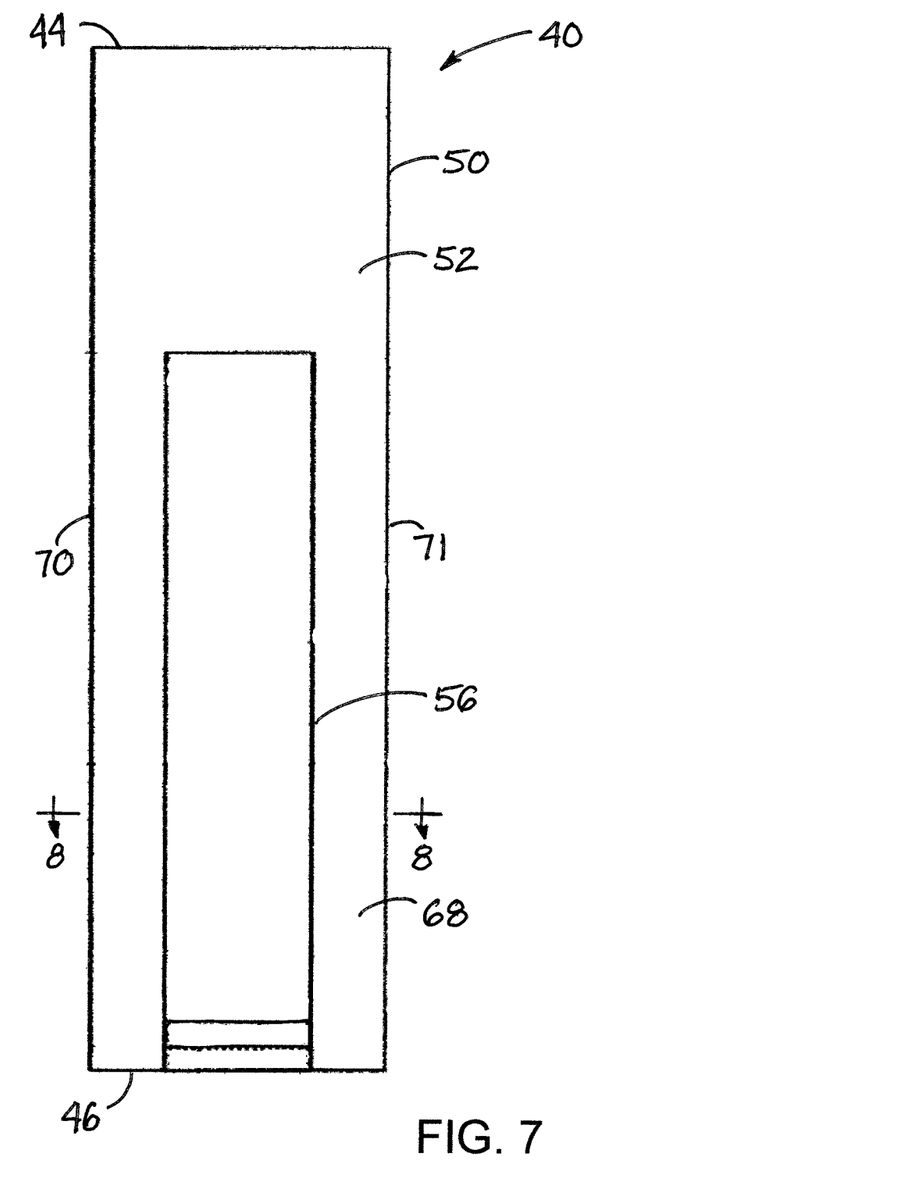
FIG. 7 is a schematic front view of an embodiment of the holder.
Figure 8A:
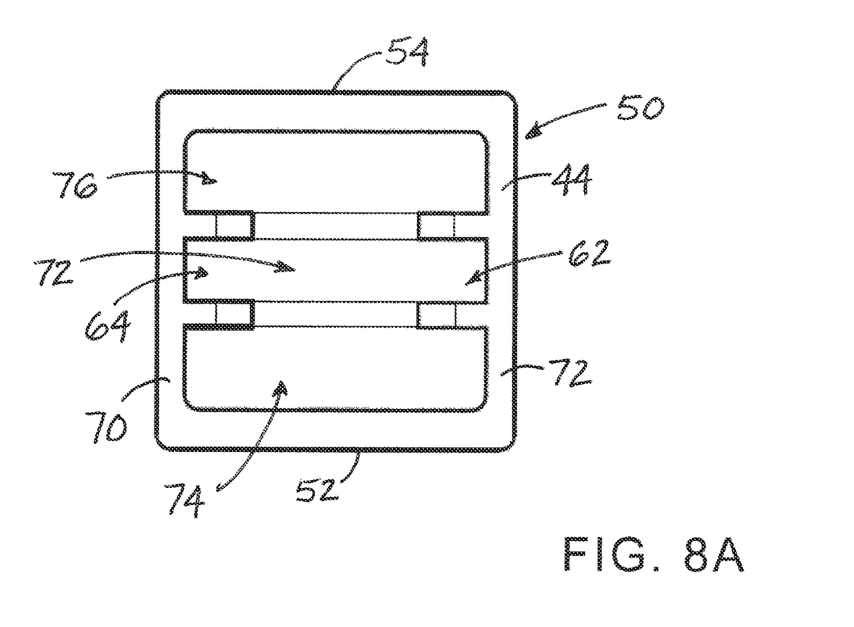
FIG. 8A is a schematic top view of an embodiment of the holder.
Figure 8B:
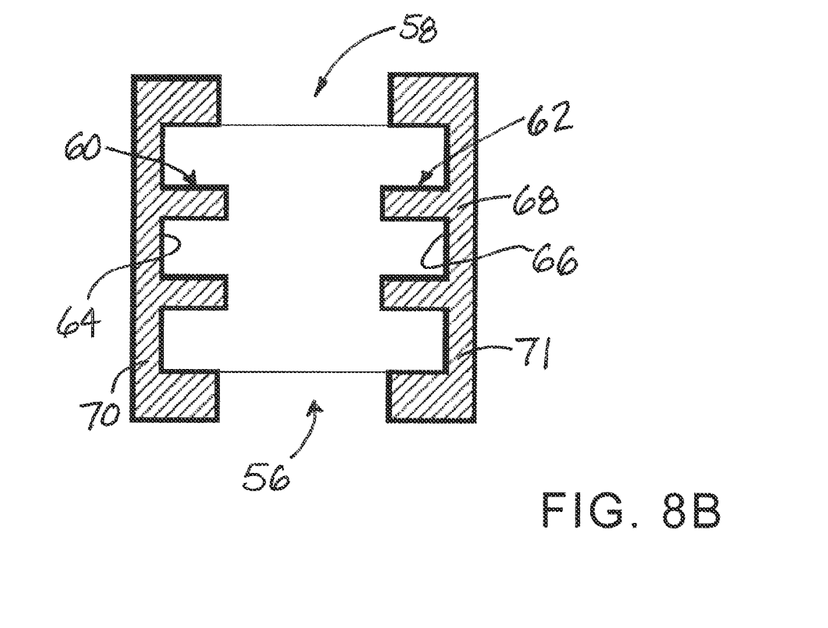
FIG. 8B is a schematic sectional view of an embodiment of the holder taken along line 8-8 of FIG. 7.
Figure 9:
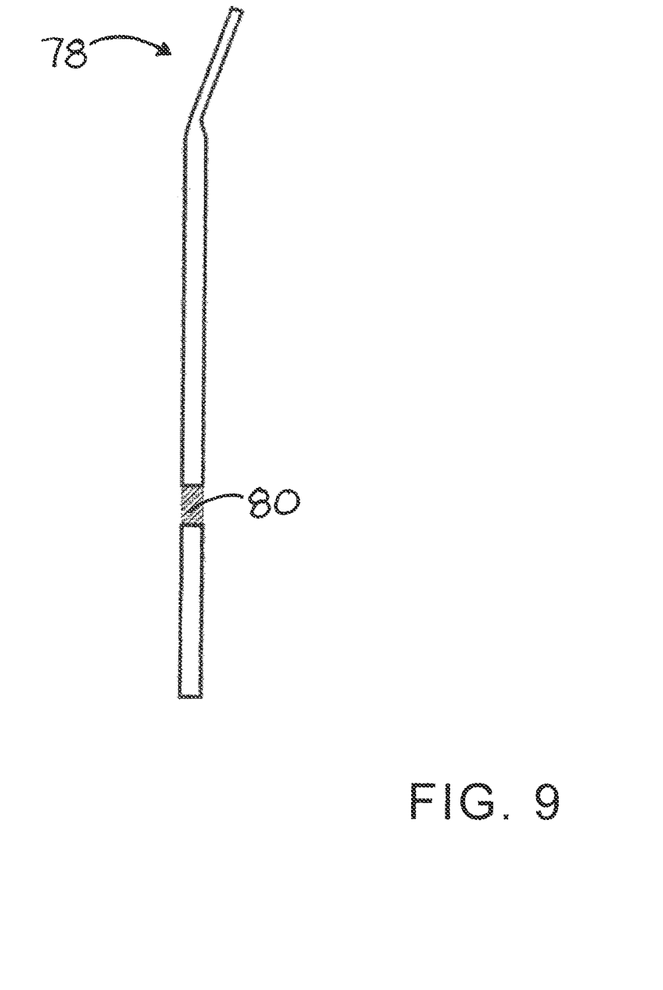
FIG. 9 is a schematic side view of an embodiment of a filter strip.

The holder 40 may have an open top end 44 and may also have a substantially closed bottom end 46. The holder may also have a perimeter wall 50 generally extending between the top end 44 and bottom end 46. The perimeter wall may include a front wall 52 and a rear wall 54 which are positioned generally in opposition to each other with respect to the perimeter wall, and may also include opposite sidewalls 70, 71 which extend between the front and rear walls.

Figure 2:
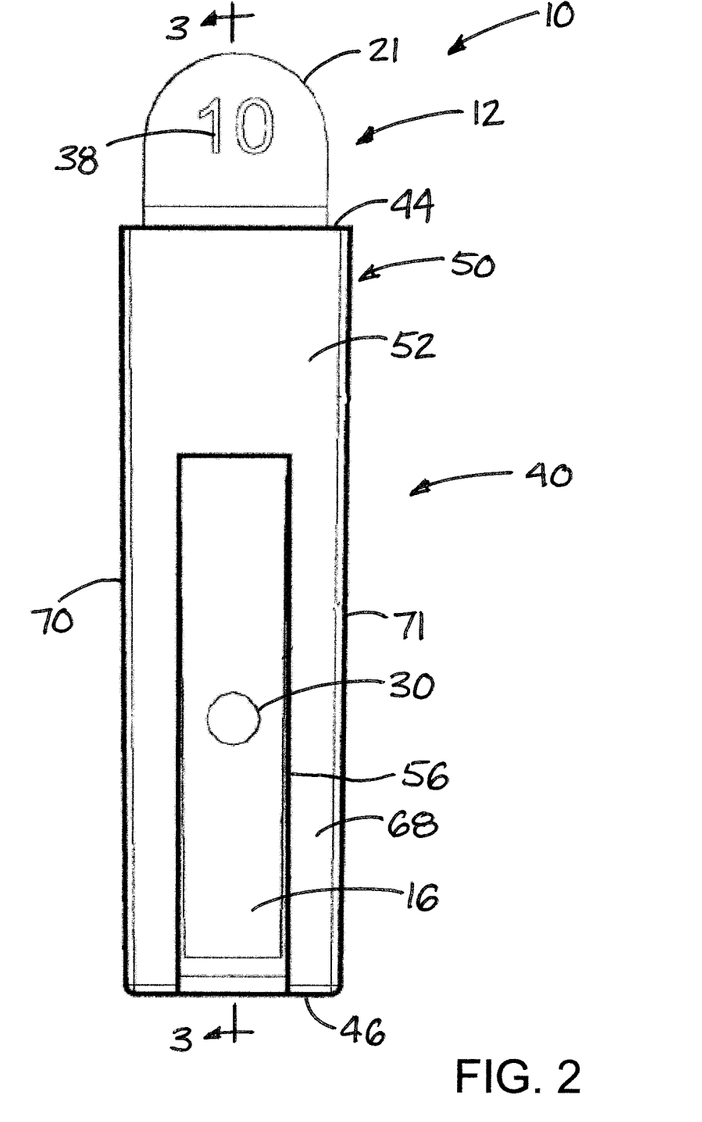
FIG. 2 is a schematic front view of the cuvette system, according to an illustrative embodiment, in an assembled condition.
Figure 3:
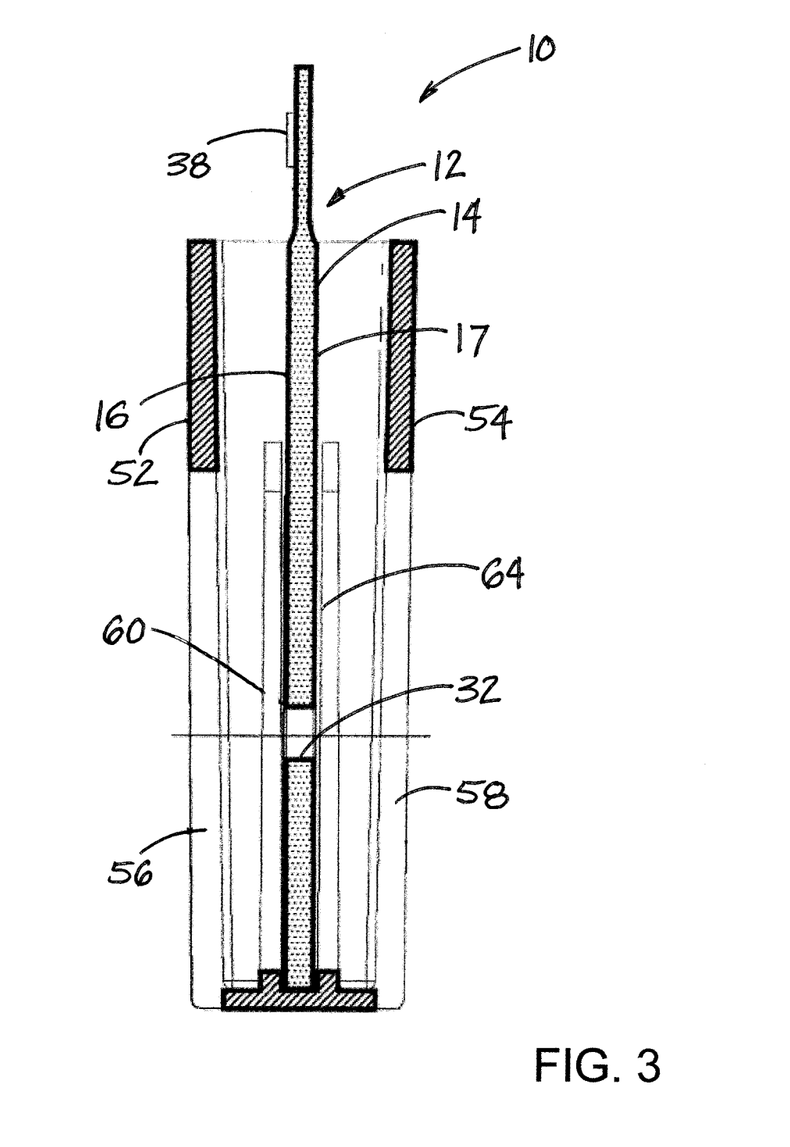
FIG. 3 is a schematic sectional view of the cuvette system, according to an illustrative embodiment, taken along line 3-3 of FIG. 2.
Figure 4A:
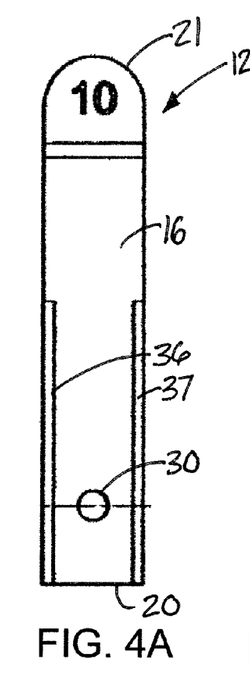
FIG. 4A is a schematic front view of an illustrative embodiment of the cuvette element, with one example of a size and a position of a hole.
Figure 4B:
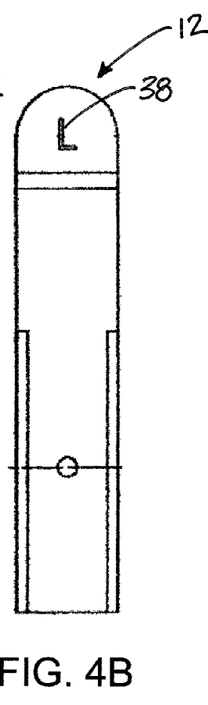
FIG. 4B is a schematic front view of another illustrative embodiment of the cuvette element, with another example of a size and a position of a hole.
Figures 4C, 4D:
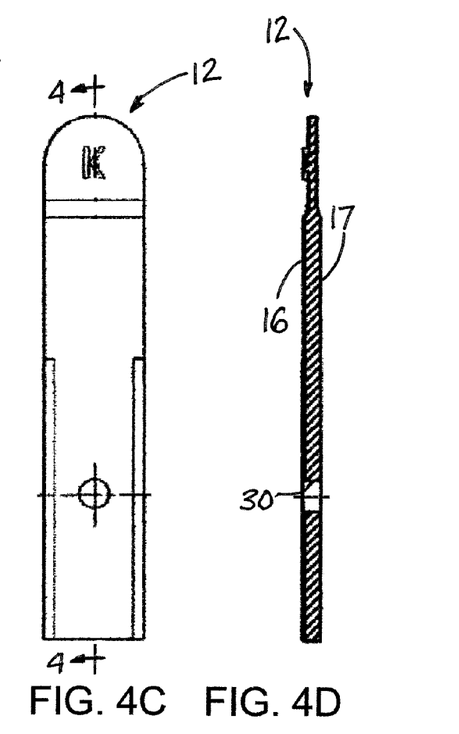
FIG. 4C is a schematic front view of still another illustrative embodiment of the cuvette element, with still another example of a size and a position of a hole.
FIG. 4D is a schematic section view of the illustrative embodiment of FIG. 4C taken along line 4-4 of FIG. 4C.
Figure 5A:
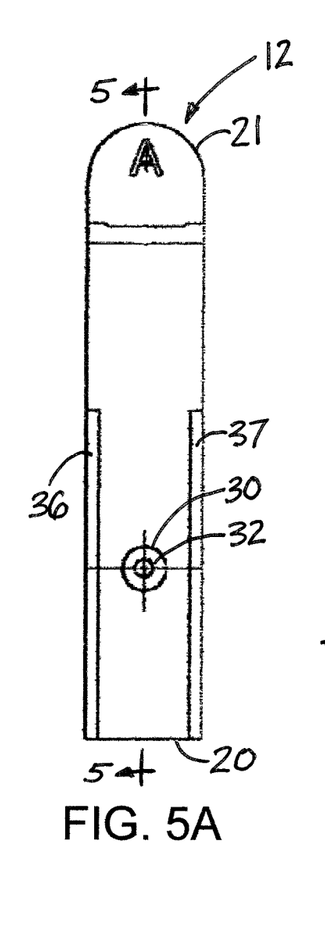
FIG. 5A is a schematic front view of an illustrative embodiment of the cuvette element, with one example of a size and shape of a well.
Figure 5B:
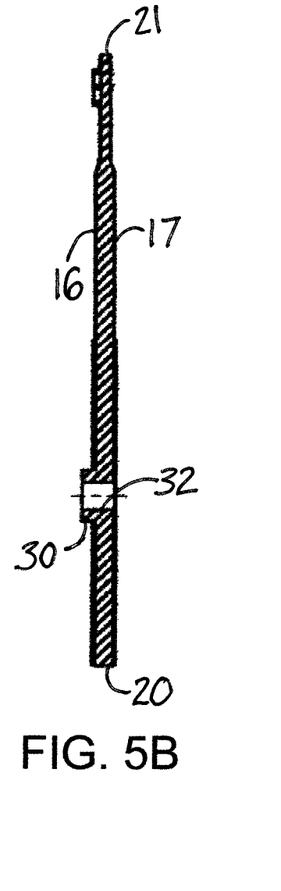
FIG. 5B is a schematic sectional view of an embodiment of the cuvette element, such as the embodiment of FIG. 5A taken along line 5-5 of FIG. 5A.
Figure 5C:
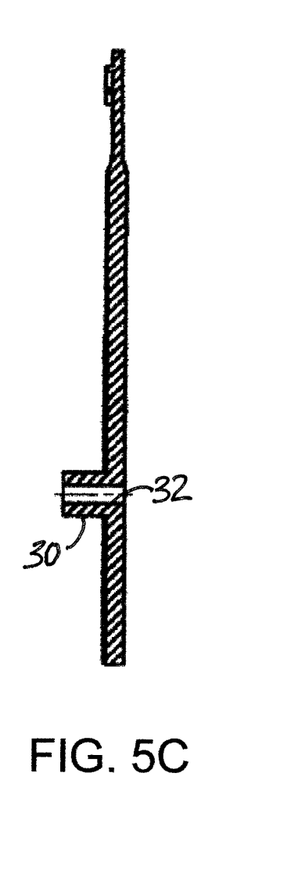
FIG. 5C is a schematic sectional view of an embodiment of the cuvette element, such as the embodiment of FIG. 5A taken along line 5-5 of FIG. 5A.
Figure 6A:
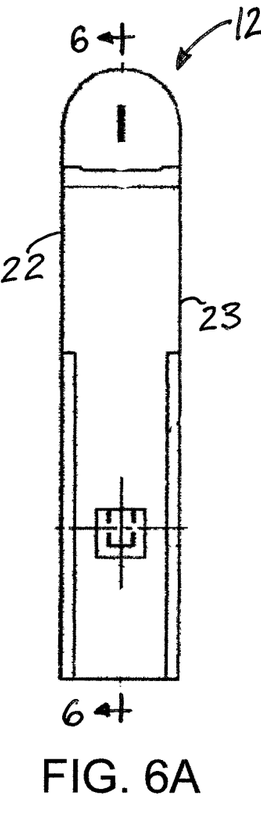
FIG. 6A is a schematic front view of an illustrative embodiment of the cuvette element, with one example of a size and a shape of a well.
Figure 6B:
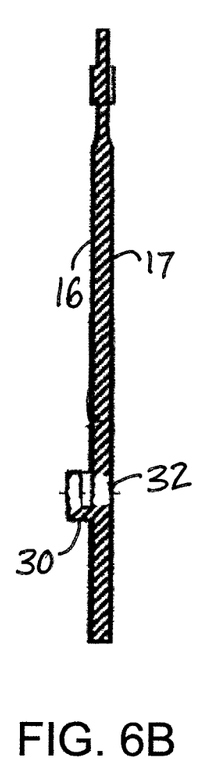
FIG. 6B is a schematic sectional view of an embodiment of the cuvette element, such as the embodiment of FIG. 6A taken along line 6-6 of FIG. 6A.
Figure 6C:
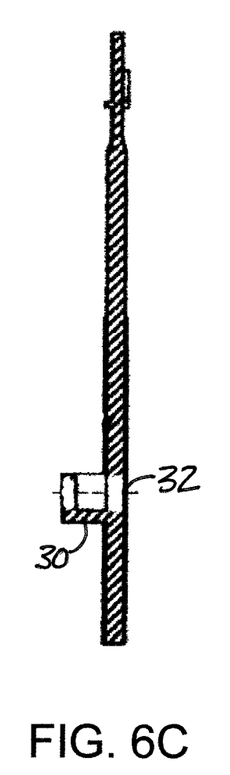
FIG. 6C is a schematic sectional view of an embodiment of the cuvette element, such as the embodiment of FIG. 6A taken along line 6-6 of FIG. 6A.

Windows 56, 58 may be formed in opposite walls of the holder, such as the front and rear walls. Illustratively, the window 56 may be formed in the front wall 52 and the window 58 may be formed in the rear wall 54. The windows 56, 58 may be generally positioned in alignment with each other, while exact registration and coextension of the windows is not required. The windows 56, 58 may be configured to be aligned with the well 30 in the cuvette element 12 when the cuvette element is inserted into the holder such that a beam of energy passing through the well 30 also passes through the windows 56, 58 so that the beam of energy does not pass through material of the cuvette element 12 or the holder 40 when the cuvette element is inserted into the holder. Thus, a straight line may be able to pass though the well 30 and the windows 56, 58 simultaneously when the element 12 is inserted into the holder 40.

The holder 40 may include at least one guide 60 that is formed in the interior of the holder, and in at least some embodiments the guide 60 includes opposing sets of guides 60, 62 that define opposing channels 64, 66 that are configured and positioned to receive the opposite side edge portions of the strip 14 of the cuvette element when the element is inserted into the interior of the holder for use. The guides 60, 62 may be formed on the interior surfaces of the side walls 70, 71 such that the strip 14 is positioned between the windows 56, 58. The channels 64, 66 may be configured to hold the cuvette element 12 in a position that is spaced from the front and the rear walls of the holder. In at least some embodiments, the exterior surface 68 of the holder has a cuboid shape with sides of generally rectangular shape, but may be configured for use in the space provided in an analysis machine for conventional cuvettes.

In the some embodiments, the guides 60, 62 and channel form a central position 72 in the interior 42 of the holder, and may also form a front position 74 between the guides and the front wall 52 of the perimeter wall. The guides may also form a rear position 76 between the guides and the rear wall 54 of the perimeter wall. The front and rear positions may be suitable for receiving a strip 14 of the type suitable for holding a sample, but in some embodiments a filter strip 78 may be positioned in one or the other of the front and rear positions in conjunction with a strip 14 in the central position. The filter strip 78 (see FIG. 9) may function to filter the beam entering the sample in the strip 14, or filter the beam leaving the sample. For example, a filter strip 78 positioned in the front position 74 may encounter the beam first and perform excitation filtering on the beam before the beam passes through the sample. As another example, a filter strip 78 positioned in the rear position 76 may encounter the beam after the beam has passed through the sample, and perform emission filtering on the beam after the beam passes through the sample. Illustratively, the filter strip 78 may be similar to the strip 14 with a window 80 of filtering material that is alignable with the well of the strip 14 when the strip is inserted into the central position. The filtering material may be selected for filtering the desired wavelength or wavelengths of energy. The strip 78 may have a bent upper tab portion that may facilitate the finger gripping of the tab portion when a strip 14 is located in the central position of the holder.

In use of the cuvette system 10, a holder 40 may be obtained and a suitable cuvette element 12 may be selected based upon, for example, the size of the sample available or the desired size of the sample to be tested. The user may select a cuvette element 12 from a plurality of cuvette elements having differently-sized wells 30, with the user selecting the cuvette element with a well that is suitably sized for the particular size of the sample to be tested. The sample material may be positioned in the well of the selected cuvette element, and the cuvette element may be inserted into the holder interior through the open top end 44 of the holder, preferably with the lower end portion of the cuvette element being inserted first into the interior. The cuvette element may be inserted into the holder at least until the well 30 is positioned between the windows 56, 58 of the holder. When the cuvette element 12 is fully inserted into the holder 40, a portion of the element 12 may protrude from the top end 44 of the holder to provide a location on the element 12 for the user to grip the element 12 with his or her fingers in order to be able to remove the element 12 from the holder after testing. The assembled holder and element may be inserted into the testing apparatus, and the test may be conducted. After the testing has been concluded, the cuvette system 10 may be removed from the analysis machine and the cuvette element 12 may be removed from the holder and element 12 may be discarded in a suitable manner while the holder 40 may be retained for future use with another cuvette element 12 as well as a different sample.

It should be appreciated that in the foregoing description and appended claims, that the terms "substantially" and "approximately," when used to modify another term, mean "for the most part" or "being largely but not wholly or completely that which is specified" by the modified term.

It should also be appreciated from the foregoing description that, except when mutually exclusive, the features of the various embodiments described herein may be combined with features of other embodiments as desired while remaining within the intended scope of the disclosure.

Further, those skilled in the art will appreciate that the steps described and shown in the disclosure may be altered in a variety of ways. For example, the order of the steps may be rearranged, substeps may be performed in parallel, shown steps may be omitted, or other steps may be included, etc.

With respect to the above description then, it is to be realized that the optimum dimensional relationships for the parts of the disclosed embodiments and implementations, to include variations in size, materials, shape, form, function and manner of operation, assembly and use, are deemed readily apparent and obvious to one skilled in the art in light of the foregoing disclosure, and all equivalent relationships to those illustrated in the drawings and described in the specification are intended to be encompassed by the present disclosure.

Therefore, the foregoing is considered as illustrative only of the principles of the disclosure. Further, since numerous modifications and changes will readily occur to those skilled in the art, it is not desired to limit the disclosed subject matter to the exact construction and operation shown and described, and accordingly, all suitable modifications and equivalents may be resorted to that fall within the scope of the claims.

I claim:
1. A cuvette system comprising:
   a disposable cuvette element for holding a sample for analysis, the cuvette element comprising an elongated strip having opposite faces; and a well for receiving the sample to be analyzed, the well being formed on the strip to hold a defined volume of a sample on the strip, a hole forming at least a portion of the well and extending through the strip; and a reusable holder for removably receiving the cuvette element, the holder having a substantially hollow interior for receiving at least a portion of the cuvette element, the holder having a perimeter wall including a front wall and a rear wall of the holder, the front and rear walls each having a window formed by a void in each of the front and rear walls the windows being generally positioned in alignment with each other;

wherein the cuvette element and the holder are configured such that positioning of the cuvette element in the holder aligns the windows of the front and rear walls of the holder and the hole of the well in the cuvette element to produce a linear path for a beam of energy through the assembled cuvette element and holder that does not pass through material forming the cuvette element and does not pass through material forming the holder.

2. The system of claim 1 wherein the well is formed by a continuous wall surrounding the hole.

3. The system of claim 2 wherein the wall extends from at least one side of the strip.

4. The system of claim 2 wherein the wall is substantially cylindrical in shape.

5. The system of claim 2 wherein the wall is substantially rectangular in shape.

6. The system of claim 1 wherein the cuvette element comprising at least one rail formed on at least one of the opposite faces and protruding from said face.

7. The system of claim 6 wherein a pair of the rails are formed on one of said faces, the rails each being positioned along at least a section of opposite side edge portions of the strip.

8. The system of claim 7 wherein the rails are substantially linear.

9. The system of claim 1 wherein the cuvette element comprising a marking on the strip indicative of a volume of the well.

10. The system of claim 1 wherein the faces of the strip define a thickness therebetween, the strip having a substantially uniform thickness.

11. The system of claim 1 wherein at least one guide is formed in the interior of the holder for removably receiving a portion of the strip to guide movement of the strip in the interior of the holder.

12. The system of claim 11 wherein the at least one guide comprises opposing sets of guides that define opposing channels that receive opposite side edge portions of the strip of the cuvette element when the element is inserted into the interior of the holder.

13. The system of claim 12 wherein the channels are configured to hold the cuvette element in a position spaced from the front and rear walls.

14. The system of claim 1 wherein the holder has an open top end for receiving the cuvette element therethrough.

15. The system of claim 14 wherein the holder has a substantially closed bottom end.

16. The system of claim 1 wherein the perimeter wall includes opposite side walls extending between the front and rear walls.

17. The system of claim 1 wherein an exterior surface of the holder has a cuboid shape.

18. The system of claim 1 additionally comprising at least one filter strip configured to filter a beam of energy passing through the filter strip; and wherein the holder defines a plurality of positions in the interior of the holder for receiving the at least one filter strip adjacent to the strip of the cuvette element such that a beam of energy on the linear path for through the assembled cuvette element and holder also passes through the at least one filter strip.

19. The system of claim 1 wherein the well is formed by a continuous wall surrounding the hole, the wall extending from at least one side of the strip;

wherein a pair of rails are formed on one of said faces, the rails each being positioned along at least a section of opposite side edge portions of the strip, the rails being substantially linear;

wherein the faces of the strip define a thickness therebetween, the strip having a substantially uniform thickness;

wherein opposing sets of guides are formed in the interior of the holder for removably receiving a portion of the strip to guide movement of the strip in the interior of the holder, the sets of guides defining opposing channels to receive opposite side edge portions of the strip of the cuvette element when the element is inserted into the interior of the holder, the channels being configured to hold the cuvette element in a position spaced from the front and rear walls; and wherein the holder has an open top end for receiving the cuvette element therethrough and a substantially closed bottom end.

* * * * *